US009078845B2

(12) United States Patent
Palermo et al.

(10) Patent No.: US 9,078,845 B2
(45) Date of Patent: Jul. 14, 2015

(54) ANTI-MICROBIAL AGENT

(75) Inventors: Frank Palermo, Preston (AU); Paul Anthony Palermo, Eaglemont (AU); Trefor Morgan, Carlton (AU); Alex Wartski, St. Kilda (AU); Ronald Harding, North Warrandyte (AU); David Ernest Bird, Point Lonsdale (AU)

(73) Assignee: Kayban Pty Ltd (AU)

( * ) Notice: Subject to any disclaimer, the term of this patent is extended or adjusted under 35 U.S.C. 154(b) by 1758 days.

(21) Appl. No.: 11/814,245

(22) PCT Filed: Jan. 20, 2006

(86) PCT No.: PCT/AU2006/000068
§ 371 (c)(1),
(2), (4) Date: Apr. 22, 2008

(87) PCT Pub. No.: WO2006/089348
PCT Pub. Date: Aug. 31, 2006

(65) Prior Publication Data
US 2008/0267890 A1 Oct. 30, 2008

(30) Foreign Application Priority Data
Jan. 20, 2005 (AU) ................. 2005900247

(51) Int. Cl.
*A01N 25/34* (2006.01)
*A61K 31/045* (2006.01)
*A01N 37/06* (2006.01)
*A61K 31/202* (2006.01)

(52) U.S. Cl.
CPC .............. *A61K 31/045* (2013.01); *A01N 37/06* (2013.01); *A61K 31/202* (2013.01)

(58) Field of Classification Search
CPC ..... A61K 31/45; A61K 31/202; A01N 37/06; A01N 31/06
See application file for complete search history.

(56) References Cited

U.S. PATENT DOCUMENTS

| 5,380,757 | A | * | 1/1995 | Horrobin ..................... 514/560 |
| 5,458,889 | A | * | 10/1995 | Bourbon et al. ............. 424/673 |
| 6,036,977 | A | * | 3/2000 | Drizen et al. ................ 424/488 |
| 6,572,868 | B1 | | 6/2003 | Cope |
| 2004/0115233 | A1 | | 6/2004 | Fukumoto et al. |
| 2004/0185115 | A1 | * | 9/2004 | Pearson et al. .............. 424/522 |
| 2006/0018938 | A1 | * | 1/2006 | Neubourg .................... 424/401 |

FOREIGN PATENT DOCUMENTS

| EP | 144984 | * 11/2004 | ............ A61K 35/78 |
| GB | 2 369 997 | 6/2002 | |
| GB | 2 375 485 | 11/2002 | |
| GB | 2 414 184 | 11/2005 | |
| JP | 2003153945 | 5/2003 | |
| JP | 2005105478 | 4/2005 | |
| WO | WO 2004/096248 | 11/2004 | |
| WO | WO 2004/108107 | 12/2004 | |

OTHER PUBLICATIONS

Linolenic acid , [online], The Free Dictionary, Retrieved [Mar. 10, 2011].*
Miyazawa et al. "Components of the essential oil from *Glehnia littoalis*." *Flavour and Fragrance Journal*. vol. 16. 2001. pp. 215-218.
Basher et al. "Essential Oil and Lipids from the Cone Berries of *Juniperus seravschanica*." *Chemistry of Natural Compounds*. vol. 35. No. 4. 1999. pp. 397-400.
El-Shazly et al. "Comparative study of the essential oils and extracts of *Achilea fragrantissima* (Forssk.) Sch. Bip. and *Achillea santolina* L. (Asteraceae) from Egypt." *Pharmazie*. vol. 59. 2004. pp. 226-230.
Denton et al. "Inhibition of *Listeria* by an Unsaturated Fatty Acids." *Journal of Nutritional Medicine*. vol. 2. No. 4. 1991. pp. 383-386.
Raychowdhury et al. "Effect of an unsaturated fatty acides in growth inhibition of some penicillin-resistant and sensitive bacteria." *Journal of Applied Bacteriology*. vol. 59. 1985. pp. 183-188.
Ohta et al. "Anti Methicillin-Resistant *Staphylococcus aureus* (MRSA) Activity by Linolenic Acid Isolated from the Marine Microalga Chloroccum HS-101." *Bull. Environ. Contaim. Toxicol.* vol. 52. 1994. pp. 673-680.
Lacey et al. "Sensitivity of *Staphylococci* to fatty acides: Novel inactivation of Linolenic acid by serum." *J. Med. Microbiol.* vol. 14. 1981. pp. 41-49.
Inouye et al. "Screening of the antibacterial effects of a variety of essential oils on respiratory tract pathogens, using a modified dilution assay method." *J. Infect. Chemother*. vol. 7. 2001. pp. 251-254.
Das. "Antibiotic-like action of essential fatty acids." *Can. Med. Assoc. J.* vol. 132. 1985. pp. 1350.
Edwards-Jones. et al. "The effect of essential oils on methicillin-ressistant *Staphylococcus aureus* using a dressing model." *Burns*. vol. 30. 2004. pp. 772-777.
Carson et al., "Antimicrobial activity of the major components of the essential oil of *Melalaeuca alternifolia*", *Journal of Applied Bacteriology*, 1995, 78, 264-269.
Carson et al., "Efficacy and safety of tea tree oil as a topical antimicrobial agent", *Journal of Hospital Infection*, 1998, 40, 175-178.
Carson et al., "Mechanism of Action of *Melalaeuca alternifolia* (Tea Tree) Oil on *Staphylococcus aureus* Determined by Time-Kill, Lysis, Leakage, and Salt Tolerance Assays and Electron Microscopy", *Antimicrobial Agents and Chemotherapy*, 2002, 46, 1914-1920.
Carson et al., "*Melalaeuca alternifolia* (Tea Tree) Oil: a Review of Antimicrobial and Other Medicinal Properties", *Clinical Microbiology Reviews*, 19, 50-62.

(Continued)

*Primary Examiner* — Lezah Roberts
*Assistant Examiner* — Nannette Holloman
(74) *Attorney, Agent, or Firm* — Merchant & Gould P.C.

(57) ABSTRACT

A composition comprising a C8 to C24 polyunsaturated fatty acid such as -linolenic or ester thereof, and terpinene-4-ol or derivative thereof. The composition has activity as a broad-spectrum antibacterial composition.

14 Claims, 3 Drawing Sheets

(56) References Cited

OTHER PUBLICATIONS

Christoph et al., "In vitro Evaluation of the Antibacterial Activity of β-Triketones Admixed to Melaleuca Oils", *Planta Medica*, 2001, 67, 768-771.

Cox et al., "Interactions between components of the essential oil of *Melalaeuca alternifolia*", *Journal of Applied Microbiology*, 2001, 91, 492-497.

Loughlin et al., "Comparison of the cidal activity of tea tree oil and terpinen-4-ol against clinical bacterial skin isolates and human fibroblast cells", *Letters in Applied Microbiology*, 2008, 46, 428-433.

Mikus et al., "In vitro Effect of Essential Oils and Isolated Mono- and Sesquiterpenes on *Leishmania major* and *Trypanosoma brucei*", *Planta Medica*, 2000, 66, 366-368.

Barel et al., "The antimicrobial activity of the essential oil from *Achillea fragrantissima*," *J Ethnopharmacol.*, 33(1-2):187-191 (1991).

Berg et al., "Effect of Linseed Oil on Platelet Adhesiveness and Bleeding-time in Patients with Coronary Heart-Disease," *The Lancet*, 980-982 (1965).

Biju et al., "Tea Tree Oil Concentration in Follicular Casts after Topical Delivery: Determination by High-Performance Thin Layer Chromatography Using a Perfused Bovine Udder Model," *J. Pharm. Sci.*, 94(2):240-245 (2005).

Biju et al., "A validated HPTLC method for determination of tea tree oil from cosmeceutical formulations," *J. Pharm. Biomed. Anal.*, 38(1): 41-44 (2005).

Bolton et al., "Lipid Metabolism in Green Leaves of Developing Monocotyledons," *Planta*, 139: 267-272 (1978).

Brand et al., "The water-soluble components of the essential oil of *Melaleuca alternifolia* (tea tree oil) suppress the production of superoxide by human monocytes, but not neutrophils, activated in vitro," *Inflamm. Res.*, 50(4): 213-219 (2001).

Brand et al., "Tea tree oil reduces histamine-induced oedema in murine ears," *Inflamm. Res.*, 51(6): 283-289 (2002).

Brand et al., "Tea tree oil reduces the swelling associated with the efferent phase of a contact hypersensitivity response," *Inflamm. Res.*, 51(5): 236-244 (2002).

Brophy et al., "Gas Chromatographic Quality Control for Oil of *Melaleuca* Terpinen-4-ol Type (Australian Tea Tree)," *J. Agric Food Chem.*, 37(5): 1330-1335 (1989).

Budhiraja et al., "Biological Activity of *Mealeuca alternifolia* (Tea Tree) Oil Component, Terpinen-4-ol, in Human Myelocytic Cell Line HL-60," *J. Manipulative Physiol. Ther.*, 22(7): 447-453 (1999).

Calcabrini et al., "Terpinen-4-ol, The Main Component of *Melaleuca alternifolia* (Tea Tree) Oil Inhibits the In Vitro Growth of Human Melanoma CellS," *J. Invest. Dermatol.*, 122(2); 349-360 (2004).

Carson et al., "Antimicrobial activity of the major components of the essential oil of *Melaleuca alternifolia*," *J. Appl. Bacteriol.*, 78(3): 264-269 (1995).

Carson et al., "Mechanism of Action of *Melaleuca alternifolia* (Tea Tree) Oil on *Staphylococcus aureus* Determined by Time-Kill, Lysis, Leakage, and Salt Tolerance Assays and Electron Microscopy," *Antimicrob. Agents Chemother.*, 46(6): 1914-1920 (2002).

Cox et al., "Interactions between components of the essential oil of *Melaleuca alternifolia*," *J. Appl. Microbiol.*, 91(3): 492-497 (2001).

Eaton et al., "Dietary Intake of Long-Chain Polyunsaturated Fatty Acids during the Paleolithic," *Lipid*, 38: 391-398 (2004).

El-Kattan et al., "The effect of terpene enhancer lipophilicity on the percutaneous permeation of hydrocortisone formulated in HPMC gel systems," *Int. J. Pharm.*, 198(2): 179-189 (2000).

Gomes-Carneiro et al., "Mutagenicity testing of (±)-camphor, 1,8-cineole, citral, citronellal, (−)-menthol and terpineol with the *Salmonella*/microsome assay," *Mutation Research*, 416(1): 129-136 (1998).

Goodwin et al., Enhancement of Skin Penetration of Nonsteroidal Anti-Inflammatory Drugs from Extemporaneously Compounded Topical-Gel Formulations, *International Journal of Pharmaceutical Compounding*, 3(6): 496-500 (1998).

Greenberg et al., "Studies to Elucidate the Effect of Monoterpenes on Acetylcholinesterase in Two Stored-Product Insects," *International Symposium on Medicinal and Aromatic Plants*, 344; 9 pgs (1993).

Hammer et al., "Antifungal activity of the components of *Melaleuca alternifolia* (tea tree) oil," *J. Appl. Microbiol.*, 95(4): 853-860 (2003).

Hart et al., "Terpinen-4-ol, the main component of the essential oil of *Melaleuca alternifolia* (tea tree oil), suppresses inflammatory mediator production by activated human monocytes,"*Inflamm. Res.*, 49(11): 619-626 (2000).

Hausen et al., "Degradation Products of Monoterpenes Are the Sensitizing Agents in Tea Tree Oil," *American J Contact Dermatitis*, 10(2): 68-77 (1999).

Kahlil et al., Regulation of Wheal and Flare by Tea Tree Oil: Complementary Human and Rodent Studies, *J. Invest. Dermatol*, 123(4): 683-690 (2004).

Knight et al. "*Melaleuca* oil (tea tree oil) dermatitis,"*J. Am. Acad. Dermatol.*, 30(3): 423-427 (1994).

Lahlou et al., "Antihypertensive effects of the essential oil of *Alpinia zerumbet* and its main consitituent, terpinen-4-ol, in DOCA-salt hypertensive conscious rats,"*Fundam. Clin. Pharmacol.*, 17(3): 323-330 (2003).

Lahlou et al., "Cardiovascular Effects of the Essential Oil of *Alpinia zerumbet* Leaves and its Main Constituent, Terpinen-4-ol, in Rats: Role of the Autonomic Nervous System,"*Planta Med.*, 68(12): 1097-1102 (2002).

Longbottom et al., "Tolerance of *Pseudomonas aeruginosa* to *Melaleuca alternifolia* (tea tree) oil is associated with the outer membrane and energy-dependent cellular process," *J. Antimicrob. Chemother.*, 54(2): 386-392 (2004).

Magnusson et al., "Terpene-enhanced Transdermal Permeation of Water and Ethanol in Human Epidermis," *Acta Dermato Venereologica*, 77(4): 264-267 (1997).

Matsunaga et al., "Isolation of the Antiulcer Compound in Essential Oil from the Leaves of *Cryptomeria japonica*," *Biol. Pharm. Bull.*, 23(5): 595-598 (2000).

Meyer et al., "Dietary Intakes of Food Sources of Omega-6 and Omega-3 Polyunsaturated Fatty Acids," *Lipids*, 38: 391-398 (2003).

Mikus et al., "In vitro Effect of Essential Oils and Isolated Mono- and Sesquiterpenes on *Leishmania major* and *Trypanosoma brucei*" *Planta Med.*, 66(04): 366-368 (2000).

Mills et al., "Inhibiton acetylcholinesterase by Tea Tree Oil" *J. Pharm. Pharmacol.*, 56(3): 375-379 (2004).

Nascimento et al., "Terinen-4-ol;mechanisms of relaxation on rabbit duodenum" *J. Pharm. Pharmacol.*, 57(4): 467-474 (2005).

Opdyke et al., "4-Terpinenol," *Food Cosmet Toxicol.*, 20: 833-834 (1982).

Pereira et al., "The α-linolenic Acid Content of Green Vegetables Commonly Available in Australia," *Int. J. Vitam. Nutr. Res.*, 71(4): 223-228 (2001).

Pongprayoon et al., "Topical anti-inflammatory activity of the major lipophilic constituents of the rhizome of *Zingiber cassumunar*. Part I: The essential oil," *Phytomedicine*, 3(4): 319-322 (1997).

Raman et al., "Antimicrobial effects of tea-tree oil and its major components on *Staphylococcus aureus*, *Staph. epidermidis* and *Propionibacterium acnes*," *Lett. App. Microbiol.*, 21(4): 242-245 (1995).

Schilcher et al., "Untersuchungen auf mögliche nephrotoxische Wirkungen von aetherischem Wacholderbeeröl (The potential nephrotoxic effects of essential juniper oil)," *Arzneimittelforschung*,47(7): 855-858 (1997), Abstract.

Southwell et al., "Skin Irritancy of Tea Tree Oil," *J. Essent. Oil Res.*, 9(1):47-52 (1997).

Walton et al.. "Acaricidal Activity of *Melaleuca alternifolia* (Tea Tree) Oil," *Arch Dermatol.*, 140(5): 563-566 (2004).

Miyazawa et al., "Inhibition of Acetylcholinesterase Activity by Monoterpenoids with a *p*-Menthan Skeleton," J. Agric. Food Chem., 45: 677-679 (1997).

\* cited by examiner

ANTI-MICROBIAL AGENT

RELATED APPLICATIONS

The present application claims priority from Australian Provisional Application No. 2005900247, the entirety of which is incorporated by reference.

FIELD

The present invention relates to anti-microbial agents. In particular, the present invention relates to broad spectrum anti-microbial agents.

BACKGROUND

Microorganisms which are resistant to anti-microbial agents are becoming an increasing problem around the world. For example, methicillin-resistant strains of Staphylococcus aureus (MRSA—also referred to as "golden staph") are now multi-resistant to antibiotics and recent isolates show increasing resistance to antibiotics such as Gentamicin, Chloramphenicol, Fusidic Acid, and Rifampicin. Only Vancomycin can currently be relied on for empirical treatment. There is considerable concern that the increasing use of Vancomycin will select Vancomycin-resistant strains of MRSA so that in the near future there may no longer be any effective antibiotic therapy against hospital staphylococci. Accordingly, investigations are underway to identify alternative anti-microbial agents, particularly broad spectrum anti-microbial agents.

Hospitals are examples of environments where MRSA acquired infections are a significant problem. These infections put the patient at risk, increase the cost of care, and reduce the number of beds available. In other environments such as dental rooms, laboratories, food preparation areas, schools and so forth, it is also important to prevent or minimise the growth of such bacteria, together with other microbial agents including fungi and viruses.

Hospitals and these other environments requiring high levels of hygiene have a range of strategies to minimise the spread of such microorganisms. Prior to entering into surgery, patients are topically treated with antiseptic solutions such as chlorhexidine or povidone iodine. Carriers of MRSA are treated with such topical antiseptics, or in severe cases, are treated with antibiotics such as Vancomycin. Vancomycin is expensive to administer, and therefore effective, less expensive orally deliverable replacements would be welcomed.

The known topical antiseptics cannot be relied upon to provide sufficient protection from such bacteria, especially as more resistant strains develop. They are also not capable of being applied in other presentation forms, such as oral tablets. Such topical antiseptics also may not be effective in preventing or inhibiting the growth of other classes of microorganisms that are present in hospitals and other such environments. Although surfaces in these environments are washed down with sterilising agents and disinfectants including bleaches containing chlorine in the form of hypochlorous acid/hypochlorite ion, these agents are quite corrosive, and other alternatives are desirable.

Accordingly, there is a need for new antimicrobial and/or antibacterial agents suitable for use in these and similar applications.

All references, including any patents or patent application, cited in this specification are hereby incorporated by reference to enable full understanding of the invention. Nevertheless, such references are not to be read as constituting an admission that any of these documents forms part of the common general knowledge in the art, in Australia or in any other country. The discussion of the references states what their authors assert, and the applicants reserve the right to challenge the accuracy and pertinency of the cited documents.

SUMMARY

In a first aspect, there is provided a method of preventing or inhibiting growth of bacteria, the method comprising the step of contacting a surface with a composition comprising a C8 to C24 polyunsaturated fatty acid or an ester thereof, and terpinen-4-ol or a derivative thereof.

It has been found by the present applicant that a-linolenic acid, which is a C8-C24 polyunsaturated fatty acid, is effective in preventing or inhibiting the growth of bacteria. The activity of this pure a-linolenic acid is similar to polyunsaturated fatty acids closely related to a-linolenic acid, as described in further detail below. α-linolenic acid has been found to be effective in preventing or inhibiting the growth of Gram negative and Gram positive bacteria and given this activity against a range of microbes, it is an effective broad-spectrum antimicrobial agent.

The present applicants have found that when the fatty acid or ester is used in combination with terpinen-4-ol or a derivative thereof (namely another derivative of terpinene), synergistic antimicrobial activity is achieved. Moreover, such a composition has activity against a broader range of microorganisims, including fungi. Indeed, test results show that compositions containing both components have around ten times the activity of compositions containing one component alone.

The surface is suitably contacted with a composition comprising terpinen-4-ol or a derivative thereof together with, prior to or following contact with the C8 to C24 polyunsaturated fatty acid or ester composition within a timeframe to obtain the synergistic effect. Preferably, the surface is contacted with a composition comprising both the C8 to C24 polyunsaturated fatty acid or ester and terpinen-4-ol or a derivative thereof, such that the time of contact is contemporaneous.

Without wishing to be bound by theory, it is believed that the C8 to C24 polyunsaturated fatty acid or ester thereof exerts its anti-microbial effect on the inside of the microorganism by destroying fatty acid metabolism, while visual observation suggests that terpinen-4-ol and derivatives thereof attack the microbe's cell wall.

Accordingly, these active agents act via different mechanisms and thus there is a reduced chance of a particular microorganism developing resistance to both of the agents. Moreover, both the C8 to C24 polyunsaturated fatty acid or ester thereof and terpinen-4-ol (or derivative) are volatile agents and therefore are less likely to remain in contact with a microorganism for an extended period of time, thereby further reducing the chance of a microorganism developing resistance to the agents.

According to a second aspect, there is also provided a composition comprising a C8 to C24 polyunsaturated fatty acid or ester thereof, and terpinen-4-ol or derivative thereof. Preferably the C8 to C24 polyunsaturated fatty acid or ester thereof is a-linolenic acid, and most preferably the a-linolenic acid is in substantially pure form (as defined below). Preferably, the composition comprises terpinen-4-ol. Preferably, the terpinen-4-ol is in substantially pure form (as defined below). The composition may be in a wide range of presentation forms, including the forms of a body wash, surface spray, a towelette, topical ointment, or nasal ointment, tablet or otherwise.

In a third aspect, there is provided a method of preventing or inhibiting growth of both Gram positive and Gram negative bacteria on a surface, the method comprising the step of contacting a surface with a composition comprising a C8 to C24 polyunsaturated fatty acid or ester thereof, and terpinen-4-ol or a derivative thereof.

In a fourth aspect, there is provided a use of a C8 to C24 polyunsaturated fatty acid or ester thereof and terpinen-4-ol or a derivative thereof in the manufacture of a composition for preventing or inhibiting growth of bacteria. Preferably the composition is a composition for preventing or inhibiting growth of Gram positive and Gram negative bacteria.

In a fifth aspect, there is provided a method of preventing or treating a disease or condition caused by bacteria, the method comprising the step of administering to a subject in need thereof a composition comprising a C8 to C24 polyunsaturated fatty acid or ester thereof, terpinen-4-ol or a derivative thereof, and a carrier. The mode of administration is preferably topical.

The composition may further comprise one or more other active agents. However, according to some embodiments, the only active agents present are the C8 to C24 polyunsaturated fatty acid or ester thereof, and terpinen-4-ol or derivative thereof.

BRIEF DESCRIPTION

DETAILED DESCRIPTION

Figure 1:
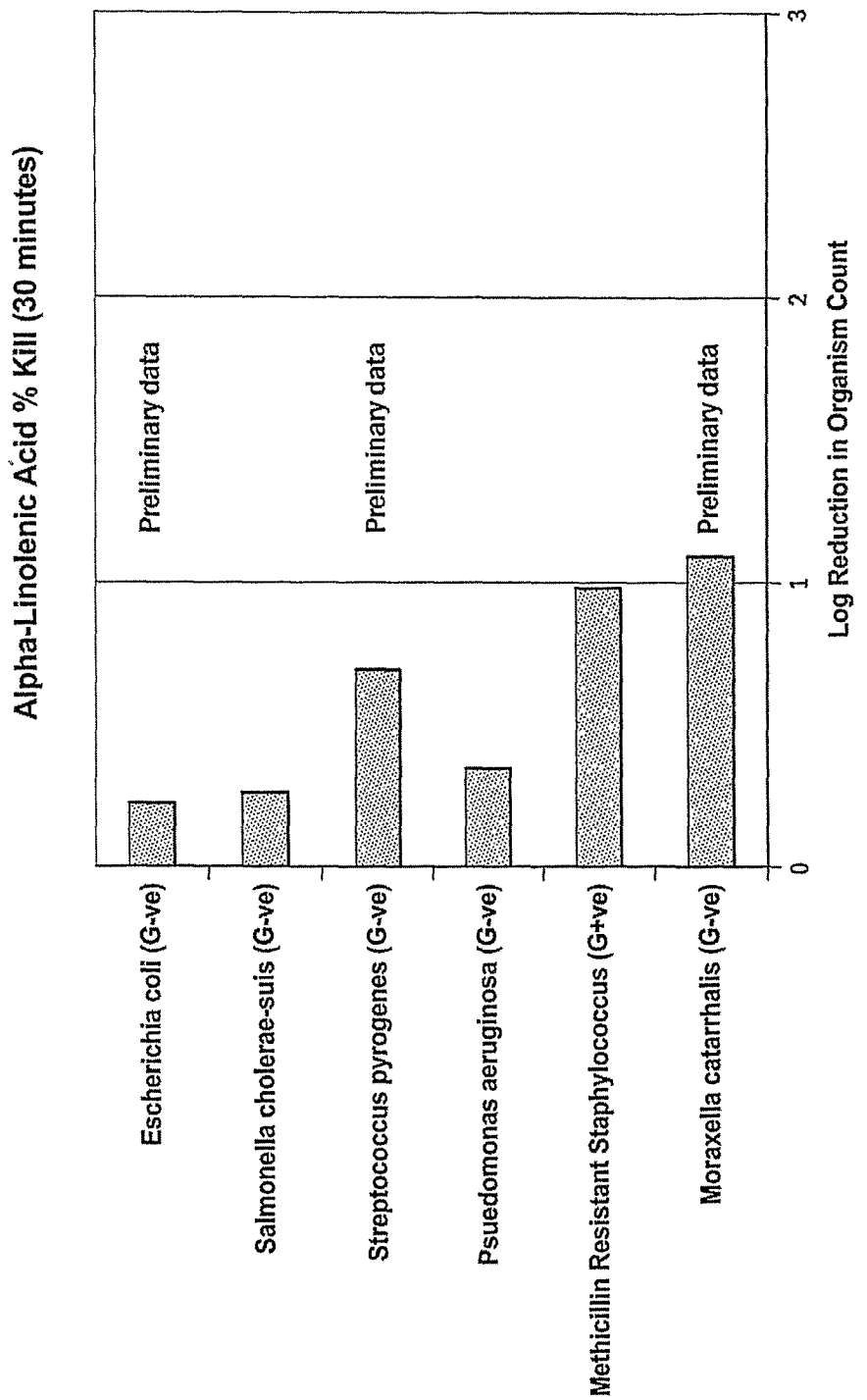
FIG. 1 is a graph of the log reduction in organism count for a number of microorganisms contacted with a-linolenic acid after 30 minutes.

In the specification, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein, the singular forms "a", "an", and "the" include the corresponding plural reference unless the context clearly dictates otherwise. Thus, for example, a reference to "a virus" includes a'plurality of viruses. Similarly, a reference to "a terpinen-4-ol or a derivative thereof" includes a mixture of more than one compound within this class.

Compositions comprising a C8 to C24 polyunsaturated fatty acid or ester thereof and terpinen-4-ol or a derivative thereof have been found by the inventors to have broad antimicrobial activity, including activities against Gram-positive and Gram-negative bacteria, including aerobic, anaerobic, and facultative aerobic bacteria. This broad activity provides wide application for the composition. It has also been found that the composition can be used in different forms, which further enhances the applications of the composition. It has been surprisingly found that a synergistic activity is provided when the C8 to C24 polyunsaturated fatty acid or ester thereof is administered with terpinen-4-ol or a derivative thereof. In addition, the combination composition has activity against a broader range of microorganisms including the Gram-positive and Gram-negative bacteria described above, and fungi.

C8 to C24 Polyunsaturated Fatty Acids

It is explained above that the preferred form of C8 to C24 polyunsaturated fatty acid or ester thereof is a-linolenic acid. α-linolenic acid is present in the form of the corresponding glyceride in linseed and other oils, and is usually present in such oils as one of several C8 to C24 polyunsaturated fatty acid components. α-linolenic acid is a C18 fatty acid containing three double bonds (C18:3) at the 9-, 12- and 15-positions.

Although the composition in its broadest aspect may comprise a mixture of C8 to O24 polyunsaturated fatty acids or esters thereof, it preferably is not present as a component of linseed oil or hydrolysed linseed oil. Preferably, it is used in the composition in purified or extracted form. Thus, preferably the composition used according to the present application comprises a single C8-C24 polyunsaturated fatty acid at a level that is substantially free of other C8-C24 polyunsaturated fatty acids. Most preferably, the composition comprises a-linolenic acid, substantially free of any other C8 to C24 saturated, mono or polyunsaturated fatty acids or esters thereof. By substantially free, it is meant that such components (that the composition is substantially free of) are not present at a level of more than 20% (on a weight to weight basis) of the single fatty acid present, such as α-linolenic acid.

C8 to C24 polyunsaturated fatty acid refers to straight chain or branched alkenyl carboxylic acids containing at least 2 degrees of unsaturation, and a hydrocarbon chain length of between 8 and 24 carbon atoms. Preferably the fatty acid is a C18 fatty acid, and more preferably it contains three degrees of unsaturation. Preferably the fatty acid is a cis-fatty acid.

The esters of such fatty acids encompass the class of compounds that can be produced by the reaction of such fatty acids with any aliphatic or aromatic organic alcohol. It is noted that such products need not be the direct product of such a reaction, and may be formed or derived from different starting materials. The alcohol may for instance be a polyol such as a diol or triol, and may contain any other functional groups. The alkyl esters are most typical.

Terpinen-4-ol and Derivatives Thereof

The C8 to C24 polyunsaturated fatty acid is used in combination with terpinen-4-ol or a derivative thereof.

Terpinen-4-ol is a component of tea tree oil. One commercially available terpinen-4-ol mixture derived from tea tree oil is known by the trade mark Melaleucol. The structure of one principal isomer of terpinen-4-ol is as follows:

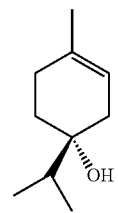

The term terpinen-4-ol encompasses single isomers such as that illustrated above or any other individual isomers and mixtures of isomers including the racemic mixture. Generally extracts of terpinen-4-ol from tea tree oil are in the form of an isomeric mixture of the (+) and (−) enantiomers in a ratio of between 1.8-2.4:1.

Terpinen-4-ol is a 3-hydrogeno 4-hydroxy containing derivative of terpinene. The derivatives of terpinen-4-ol encompassed by the present application are the other derivatives of terpinene in which one or both double bonds are saturated, and the compound is substituted with one or more substituents selected from hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, and phosphorus-containing groups. Terpinen-4-ol is the derivative containing hydrogen and hydroxy substitution across the saturated C3-4 double bond of terpinene.

Preferably, however, terpinen-4-ol (including isomeric mixtures thereof) is used in a substantially pure form. The expression "substantially pure form" means that the terpinen-4-ol, or derivative thereof, is used in a form that is substantially free of the other principal components of tea tree oil. In this context, substantial means that the terpinen-4-ol used in the composition contains no more than 20% (weight to weight) of the non-terpinen-4-ol components of tea-tree oil. Thus, this level covers pure terpinen-4-ol extracts, and extracts retaining small levels of impurities from tea-tree oil. Of course, the terpinen-4-ol or derivative thereof may be produced synthetically, in which case it would not be expected that any of the non-terpinen-4-ol components of tea-tree oil would be present.

Components of Compositions

The C8-C24 polyunsaturated fatty acid-containing compositions used in accordance with the present invention preferably comprise between 0.1% to 50% by weight C8-C24 polyunsaturated fatty acid. More preferably, the composition comprises or is applied at a concentration of between 0.1 and 20% w/w, depending upon the form of the composition and its route of administration. At levels below 0.1%, the effectiveness of the composition is not as high as would be desired for a commercially acceptable product. At levels above 50% the C8-C24 polyunsaturated fatty acid such as a-linolenic acid is likely to cause skin irritation or be difficult to handle. Generally for presentations suitable for direct skin applications the level of C8-C24 polyunsaturated fatty acid will be lower than this—generally at a level of not more than 10%. A good balance between antimicrobial properties, ease of use and cost is obtained for compositions comprising between 0.1% and 5% C8-C24 polyunsaturated fatty acid, and particularly a-linolenic acid.

The composition preferably comprises between 0.1% and 5% terpinen-4-ol or a derivative thereof, more preferably between 0.25% and 5% terpinen-4-ol or a derivative thereof. Preferably, the terpinen-4-ol itself in a substantially pure form is present in the composition at the given levels.

For compositions comprising both C8-C24 polyunsaturated fatty acid or ester thereof (preferably a-linolenic acid in substantially pure form), together with terpinen-4-ol or a derivative thereof (preferably terpinen-4-ol in substantially pure form), the ratio of these two components in the composition is advantageously between 1:5 and 5:1, more preferably between 1:2 and 2:1.

The compositions of the present invention will generally further comprise a carrier. Depending on the presentation form, the carrier may be a pharmaceutical carrier, or it may be a more general carrier.

Pharmaceutical carriers for preparation of pharmaceutical compositions are well known in the art, as set out in textbooks such as Remington's Pharmaceutical Sciences, 20th Edition, Williams & Wilkins, Pennsylvania, USA. The carrier will depend on the route of administration, and again the person skilled in the art will readily be able to determine the most suitable formulation for each particular case.

Examples of different presentation forms are lotion, suspension, solution, spray, emulsion, paste, foam, eyewash, ointment, liquid soap, cream, solid soap, mouthwash, pastille or lozenge, gel, a towelette, hair tonic, shampoo or jelly.

In the case where the composition is in the form of a surface spray, the carrier is suitably water, and the composition may further comprise preservative such as benzyl alcohol (for example, in an amount of from 0.1-5 wt %), cosolvents such as propylene glycol (for example, in an amount of from 1-20 wt %), and surfactants such as Cremophor Rh40 (for example, in an amount of from 1-20 wt %).

In the case where the composition is in the form of a lotion or body wash, it may comprise an emulsion of C8-C24 polyunsaturated fatty acid or ester, and optionally terpinen-4-ol, in water in the presence of a suitable emulsifying agent. Examples of suitable emulsifying agents are cetosteryl alcohol, Emulgade, SLEX (Texapon), Betaine derivatives such as the Empigen B__ range of surfactants, and Tween (eg Tween 80® ICI Chemicals). Tween 800 is a surfactant which includes polyoxyethylene 20 sorbitan mono-oleate. The composition may further comprise emollients and fragrances (including oils such as sweet almond oil), preservatives (such as benzyl alcohol at levels of, for instance, 0.1-10%) and humectant and/or emollient and/or excipients (such as glycerol, for instance at levels of 0.5-10% and cyclomethicone at levels of between 0.1-20%).

When the composition is in the form of a moistured towelette it may come comprise carriers, preservatives, emulsifiers, emollients and/or fragrances as described above.

When the composition is in the form of an ointment, it may comprise a conventional ointment base to which the active ingredient is added. The ointment base may be a paraffin, such as soft paraffin, or a combination of soft and liquid paraffin. Other ointment bases may also be used such as polyalkylene glycol (such as polyethylene or polypropylene glycol) base. Other possible components of an ointment composition include emulsifying wax (for example, in an amount of between 1-40%, preferably 5-40%), and preservative.

When the composition is in the form of a liquid soap, any known liquid soap may be used. A preferred liquid soap is a coconut oil-based liquid soap. The pH of the liquid soap base may be adjusted to that which is suitable for topical use.

When the composition is a cream, any suitable cream base may be used. A preferred cream base is sorbolene cream. Other cream bases may also be used.

When the composition is in the form of a solid soap, it is preferred that a synthetic soap base is used. Synthetic soap bases are preferred because their properties are more suitable for sustained application to debilitated skin and their pH is more readily controlled. Examples of synthetic soap bases suitable for use in a composition of the invention include Synbase A and Synbase BW available from Witco (USA), Synbase Commercial Bar from Dove (USA), Tensia from Dermactif (Belgium) and pH 6-7 Syndet Base from Zetesap (Germany). An as example of the constituents of such soap bases, Syndbase BW comprises disodium myristanido MEA sulphosuccinate, stearic acid, sodium cocyl isethianate, paraffin, PEG 75, zinc stearate, and water.

When the composition is in the form of a lozenge, it may comprise a flavoured base, such as sucrose and acacia or tragacenth gum.

When the composition is in the form of an eyewash, it may comprise a suitable sterile aqueous or non-aqueous vehicle.

Additives such as buffers, preservatives including bactericidal and fungicide agents, such as phenyl mercuric acetate or nitrate, benzalkonium chloride or chlorhexidine and thickening agents such as hypromellose may also be included.

In addition to any of the ingredients listed above, the composition may further comprise other agents. For example, agents such as binders, sweeteners, thickeners, flavouring agents, disintergrating agents, coating agents, preservatives, lubricants, and/or time delay agents. Suitable examples of these are well known in the art.

C18 to C24 polyunsaturated fatty acids are known to be readily oxidised by air. The present inventors have found by experience that the composition of the invention has a shelf-life of at least 2 years. This may be extended by adding an anti-oxidant to the composition.

The composition may include or be used with agents such as therapeutic agents, antiseptic agents and/or antibacterial agents. A "therapeutic agent" is an agent used to treat a disease or condition. Suitable therapeutic agents are antibiotics such as vancomycin, penicillin and related antibiotics, methicillin, gentamycin, chloramphenicol, Fusidic acid, rifampicin and so forth. Other therapeutic agents include surgical implants, prosthesis, and catheters.

Suitable antispectic or antibacterial agents include Triclosan®, Sapoderm, Chlorhexidine, Povidone-Iodine, Cetrimide, Hexachlorphene, hypochlorite-based antiseptic agents, or mixtures thereof. The other agent(s) may be present in the composition in an amount up to 20% by weight, more preferably up to 15% by weight, of the total composition. The amount of the other agent will depend upon the activity of the other agent; however, a person skilled in the art will be readily able to determine a suitable amount.

The composition of the invention preferably has a pH in the range of 4.8 to 7.5. More preferably, the pH is in the range of 5.8 to 7.0. At these pH ranges forms of the composition that can be applied to the skin cause little irritation to the skin or mucous membranes of a subject following application.

Methods

The present invention provides a method of preventing or inhibiting growth of a microorganism. As used herein "preventing" means to kill the microorganism. In contrast, "inhibiting" means to decrease, or limit the growth of the microorganism. For example, a bacteriostatic agent inhibits bacterial growth but does not kill bacteria, while a bactericidal agent kills bacteria. The compositions of the invention may be described as antibacterial agents. The compositions may be described as disinfectants when formulated for application to surfaces or for dilution in aqueous solvents. The composition may be described as an antiseptic when formulated for application to a subject, including human or non-human animals.

"Growth" means an increase in the size and/or numbers of a microorganism. The growth of a microorganism may be determined by any method known in the art, including both direct and indirect methods. For example, direct methods include measuring the numbers of microorganisms, such as by serial dilutions and plate counts. Indirect methods include estimating the number of microorganisms from the turbidity or metabolic activity of the culture. Alternatively, the dry weight of the culture may be used to determine growth of the microorganism.

A "microorganism" or "microbe" is any organism of microscopic size. Microorganisms include bacteria, viruses, fungi such as yeasts and molds, algae, and the like.

"Bacteria" are single-celled organisms which are enclosed by a cell wall and whose genetic material is not enclosed in a nuclear membrane. Bacteria may be Gram-positive or Gram-negative, aerobic, anaerobic, or facultative anaerobes, and may have one of several shapes, such as rod-like (bacillus), spherical or ovoid (coccus), corkscrew (spiral), starshaped or square shaped. Individual bacteria may form pairs, chains, clusters or other groupings.

Examples of bacteria whose growth may be prevented or inhibited according to the invention include *Escherichia coli, Klebsiella pneumoniae, Listeria monocytogenes*, methicillin-resistant, *Neisseria flavescens, Pseudomonas aeruginosa, Salmonella salford, Salmonella cholerae, Serratia marcescens, Staphylococcus aureus, Staphylococcus epidermis, Streptococcus faecalis, Streptococcus faecium* and *Moraxella catarrhalis*. Some characteristics of these bacteria are provided in Table 1.

TABLE 1

| Bacteria | Gram stain | Oxygen requirement |
|---|---|---|
| E. coli | −ve | Aerobe |
| K. pneumoniae | −ve | Aerobe |
| L. monocytogenes | +ve | Aerobe |
| MRSA | +ve | Facultative anaerobe |
| N. flavescens | −ve | Aerobe |
| P. aeruginosa | −ve | Anaerobe |
| S. Salford | −ve | Aerobe |
| S. cholerae | −ve | Aerobe |
| S. marcescens | −ve | Aerobe |
| S. aureus | +ve | Facultative anaerobe |
| S. epidermis | +ve | Aerobe |
| S. faecalis | +ve | Facultative anaerobe |
| S. faecium | +ve | Facultative anaerobe |

"Viruses" are very small, requiring an electron microscope to view, and they are not cellular. A virus particle contains a core made of only one type of nucleic acid, either DNA or RNA, which is surrounded by a protein coat. The coat may be surrounded by a lipid envelope. Viruses can only reproduce inside the cells of other organisms.

"Fungi" are microorganisms whose cells have a distinct nucleus that contains the cell's genetic material and are surrounded by a nuclear membrane. Fungi may be unicellular or multicellular. The unicellular form of fungus is yeast. Where fungi are referred to, yeast is the preferred form of fungi. Yeasts are oval-shaped microorganisms which are larger than bacteria. The most typical fungi are molds. Molds form mycelia, which are long, branched filaments that intertwine. Examples of fungi suitable for use with the invention include *A. niger* and *C. albicans*.

Growth of the microorganism is prevented or inhibited by contacting the microorganism, or a surface on which the microorganism may come in contact, with a composition comprising a C8 to C24 polyunsaturated fatty acid or ester thereof in combination with terpinen-4-ol or a derivative thereof, or by administering the composition to a subject. The contacting may be by any suitable means, and may have a direct or indirect affect on the microorganism. For example, the composition per se may affect the growth of the microorganism. Alternatively, the composition may decrease the adhesion of the microorganism to a surface or influence another component of the microorganism culture, thereby affecting the growth of the microorganism.

The surface may be any suitable surface, such as a human or animal body, or an inanimate object.

Suitably the composition is contacted with the microorganism by administering the composition topically and/or orally to a subject in need thereof. Alternatively, the composition may be applied to an inanimate surface comprising the microorganism or suspected or at risk of comprising the microorganism. The term "surface" is used in its broadest sense, and should not be read as implying any specific physical dimensions.

The composition may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The composition may be administered to a subject in need thereof periodically or repeatedly, and may be administered to the site of actual or possible infection. For example, if infection of a surgical wound has occurred or is desired to be prevented, the composition may be administered on or to the wound and around the wound. If infection of the nasal passages may occur or has occurred or is desired to be prevented, administration of the composition to the nasal passages may be appropriate, and the composition may be in the form of a nasal ointment or nasal spray. If infection of the throat has occurred or is desired to be prevented, the composition may be in the form of a throat gargle, lozenge, or spray.

A suitable prophylactic treatment regime includes washing the patient with the composition, optionally following a separate antiseptic treatment (depending on the components in the composition). This may be conducted on a periodic or repeating basis. The composition may be in the form of a body wash, or otherwise a lotion may be applied followed by gauze. The composition is allowed to dry. The procedure may be repeated a number of times a day, with three times a day being suitable. The nasal ointment or spray may also be applied.

"Disease" is a general term used to refer to any departure from health in which a subject suffers. A "condition" refers to an abnormal functioning of a function or part of a body. Examples of diseases or conditions which may be prevented or treated by the composition comprising a C8 to C24 polyunsaturated fatty acid or ester thereof include cellulitis, necrotizing subcutaneous infections such as necrotizing fasciitis, abscesses, bacterial infections, pruritus, dermatitis, eczema, psoriasis, acne, boils, bed sores, heat rash, skin blemishes, ichthyosis, tinea, and ulcers, fungal diseases, herpes i.e. cold sores, chicken pox, and shingles, and parasitic infections. The method may also be used to improve the appearance of dry, flaky, wrinkled, aged, or photodamaged skin. It may also be used to soothe or alleviate the associated effects of the disease or condition such as pain, itching, swelling, etc.

The "subject" may be a mammal. The mammal may be a human, or may be a domestic or companion animal. While it is particularly contemplated that the compounds of the invention are suitable for use in humans, they are also applicable to veterinary use, including treatment of companion animals such as dogs and cats, and domestic animals such as horses, cattle and sheep, or zoo animals such as non-human primates, felids, canids, bovids, and ungulates.

Unless otherwise indicated, the present invention employs conventional chemistry and microbiology techniques within the capacity of those skilled in the art. Such techniques are well known to the skilled worker, and are explained fully in the literature.

It is to be clearly understood that this invention is not limited to the particular materials and methods described herein, as these may vary. It is also to be understood that the terminology used herein is for the purpose of describing particular embodiments only, and it is not intended to limit the scope of the present invention, which will be limited only by the appended claims.

Where a range of values is expressed, it will be clearly understood that this range encompasses the upper and lower limits of the range, and all values in between these limits.

Although any materials and methods similar or equivalent to those described herein can be used to practice or test the present invention, the preferred materials and methods are now described in detail by way of reference only to the following non-limiting examples and drawings.

EXAMPLE 1

Minimum Inhibitory Concentration Test for α-Linolenic Acid

The following tests were conducted to determine the minimum concentration of α-linolenic acid required to inhibit growth of three strains of bacteria which are representative of microorganisms desired to be inhibited by antimicrobial compositions. The test results show that low levels corresponding to compositions having as little as 0.1%.

A sample of 90% a-linolenic acid was diluted in accordance with the following protocol to test the minimum effective concentration against the bacteria. The α-linolenic acid was diluted to the dilutions shown in Tables 2A to 2F using Tryptone Soya broth Sigma Aldrich. Each diluted sample was inoculated with approximately $10^6$ test microorganisms of the class and incubated for 48 hours at 37° C. The test microorgansisms were *S. aureus, S. cholerae*, MRSA, *E. coli, S. pyogenes* and *M. catarrhalis*. Uninoculated broth was included as a control.

Following the incubation period each broth was examined for bacterial growth, as indicated by turbidity of the broth. Samples from each broth were subcultured to confirm the presence of the test organism. The highest serial dilution which achieved inhibition of the test organism was deemed to be the minimum inhibitory concentration (MIC).

The turbidity of each serial dilution for each test organism is shown in Tables 2A, 2B, 2C, 2D, 2E and 2F.

TABLE 2A

Test Organism: *Staphylococcus aureus* ATCC 6538

| Test | \multicolumn{10}{c}{Dilution} |
|---|---|---|---|---|---|---|---|---|---|---|
| | 1:100 | 1:200 | 1:400 | 1:800 | 1:1600 | 1:3200 | 1:6400 | 1:12800 | 1:25600 | 1:51200 | 1:102400 |
| 1 | − | − | − | − | − | − | − | − | − | + | Not Tested |
| 2 | − | − | − | − | − | − | − | − | − | − | + |

TABLE 2B

Test Organism: *Salmonella cholerae-suis* ATCC 10708

| Test | \multicolumn{11}{c}{Dilution} |
|---|---|---|---|---|---|---|---|---|---|---|---|
| Test | 1:100 | 1:200 | 1:400 | 1:800 | 1:1600 | 1:3200 | 1:6400 | 1:12800 | 1:25600 | 1:51200 | 1:102400 |
| 1 | − | − | + | + | + | + | + | + | + | + | + |
| 2 | − | − | + | + | + | + | + | + | + | + | + |

TABLE 2C

Test Organism: Methicillin Resistant *Staphylococcus* Wild Strain

| Test | 1:100 | 1:200 | 1:400 | 1:800 | 1:1600 | 1:3200 | 1:6400 | 1:12800 | 1:25600 | 1:51200 | 1:102400 |
|---|---|---|---|---|---|---|---|---|---|---|---|
| 1 | − | − | − | − | − | − | − | − | − | − | + |
| 2 | − | − | − | − | − | − | − | − | − | − | + |

TABLE 2D

Test Organism: *Escherichia coli* ATCC 8739

| Test | 1:100 | 1:200 | 1:400 | 1:800 | 1:1600 | 1:3200 | 1:6400 | 1:12800 | 1:25600 | 1:51200 | 1:102400 |
|---|---|---|---|---|---|---|---|---|---|---|---|
| 1 | + | + | + | + | + | + | + | + | + | + | + |
| 2 | + | + | + | + | + | + | + | + | + | + | + |

TABLE 2E

Test Organism: *Streptococcus pyogenes* University of Melbourne MDU

| Test | 1:100 | 1:200 | 1:400 | 1:800 | 1:1600 | 1:3200 | 1:6400 | 1:12800 | 1:25600 | 1:51200 | 1:102400 |
|---|---|---|---|---|---|---|---|---|---|---|---|
| 1 | − | − | − | − | − | − | − | − | + | + | + |
| 2 | − | − | − | − | − | − | − | − | − | + | + |

Notes:
'−' indicates no growth,
'+' indicates growth.

TABLE 2F

Test Organism: *Morazella Catarrhalis*

| Test | 1:100 | 1:200 | 1:400 | 1:800 | 1:1600 | 1:3200 | 1:6400 | 1:12800 | 1:25600 | 1:51200 | 1:102400 |
|---|---|---|---|---|---|---|---|---|---|---|---|
| 1 | − | − | − | − | − | − | − | + | + | + | + |
| 2 | − | − | − | − | − | − | − | + | + | + | + |

Notes:
'−' indicates no growth,
'+' indicates growth.

EXAMPLE 2

Compositions Comprising α-Linolenic Acid

Compositions comprising 1% and 2% α-linolenic acid were prepared with the following components:

| 1% Solution: | |
|---|---|
| % | Material |
| 1 | α-linolenic acid, 90% purity, from Optigen (South Australia) |
| 3 | Cetostearyl Alcohol |
| 5 | Sweet Almond Oil |
| 10 | Emulgade N1 1000 |
| 2 | Glycerol |
| 1 | Benzyl Alcohol |
| 1 | Cyclomethicone (DC 345) |
| 10 | SLES (TEXAPON N25) |
| 10 | Betaine (Empigen BS AU) |
| 1 | Linolenic Acid |
| 56 | Purified Water |

| 2% Solution: | |
|---|---|
| % | Material |
| 2 | α-linolenic acid, 90% purity, from Optigen (South Australia) |
| 3 | Cetostearyl Alcohol |
| 5 | Sweet Almond Oil |
| 10 | Emulgade N1 1000 |
| 2 | Glycerol |
| 1 | Benzyl Alcohol |
| 1 | Cyclomethicone (DC 345) |
| 10 | SLES (TEXAPON N25) |
| 10 | Betaine (Empigen BS AU) |
| 1 | Linolenic Acid |
| 55 | Purified Water |

EXAMPLE 3

Anti-Microbial Activity of Compositions Comprising α-Linolenic Acid

The 1% solution of Example 2 was subjected to testing to show that such solutions are effective in preventing growth of both Gram positive and Gram negative bacteria.

The biocidal effect of the 1% α-linolenic acid solution was tested against MRSA (Gram positive, facultative anaerobe), *Salmonella cholerae* (Gram negative, aerobe), and *Pseudomonas aeruginosa* (Gram negative, anaerobe) using a suspension test. The suspension test was performed according to the following procedure:
1. The starting microorganism concentration was determined by standard plate count technique for each of a test microorganism culture comprising 1% α-linolenic acid and a control microorganism culture. The microorganism concentration of each culture was recorded as cfu/mL.
2. At desired time points, a sample of each culture was removed and the microorganism concentration of each culture was determined by the standard plate count technique. The concentration was recorded as cfu/mL.
3. The % kill caused by the a-linolenic acid was calculated by comparing the difference in the cfu/mL of the test microorganism over time with the difference in the cfu/mL of the control microorganism culture over the same time.

The results are presented as geometric means of duplicate tests using fresh bacterial cultures and solutions for each test, as shown in Table 3.

TABLE 3

Biocidal effect of α-linoleuic acid

| Organism | Initial Count per mL | Final Count per mL | | % Kill |
|---|---|---|---|---|
| | | 5 mins | 30 mins | |
| Methicillin Resistant *Staphylococcus* | $1.5 \times 10^7$ | $5.5 \times 10^6$ | $1.7 \times 10^6$ | 89.7 |
| *Salmonella cholerae-suis* | $3.3 \times 10^7$ | $1.8 \times 10^7$ | $1.8 \times 10^7$ | 45.5 |
| *Pseudomonas aeruginosa* | $7.1 \times 10^7$ | $3.2 \times 10^7$ | $3.2 \times 10^7$ | 54.9 |

Note:
Results are Geometric means of duplicate tests.

Figure 2:
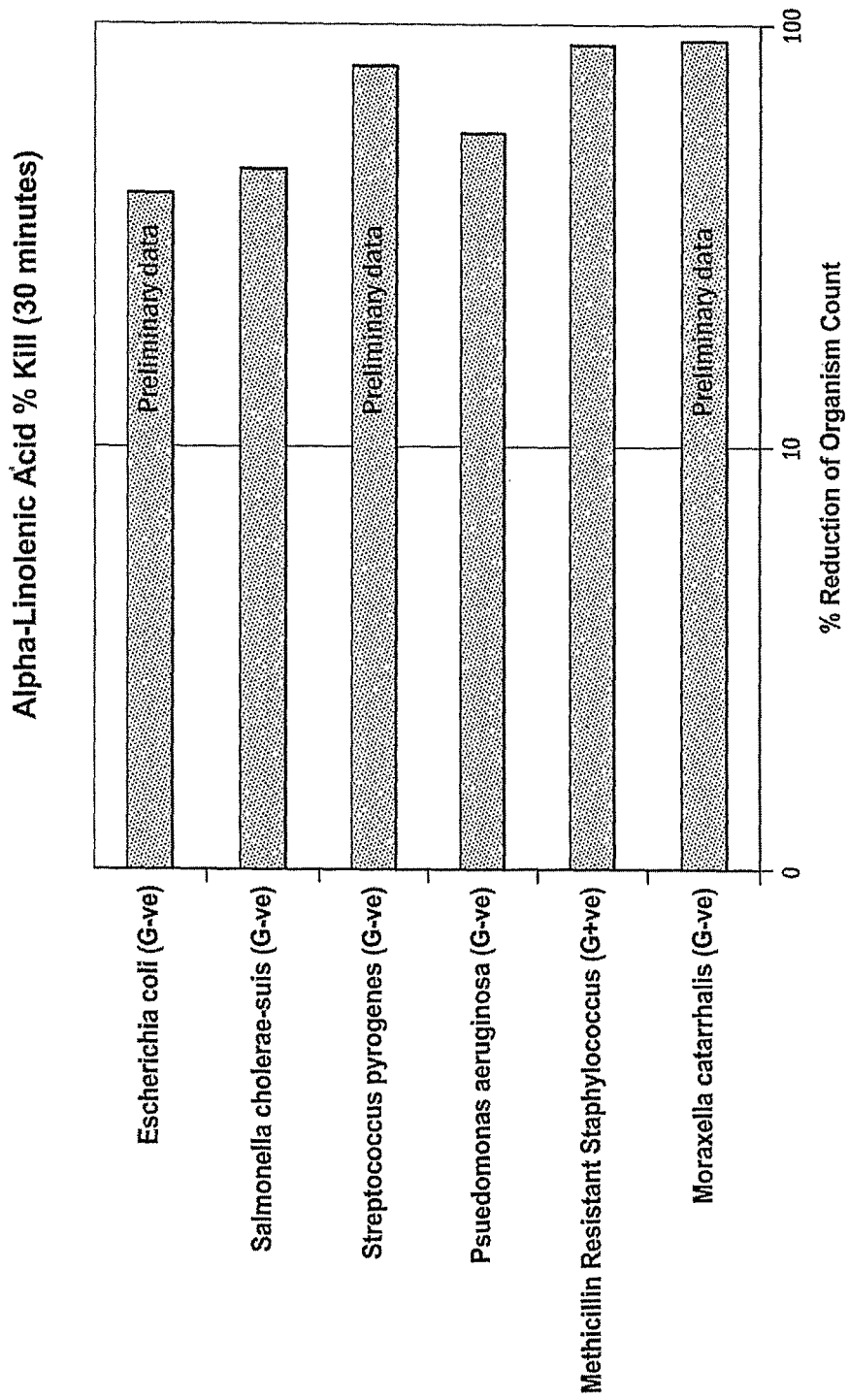
FIG. 2 is a graph showing the % reduction of organism cotnt for a number of microorganisms contacted with a composition of one embodiment of the invention.
Figure 3:
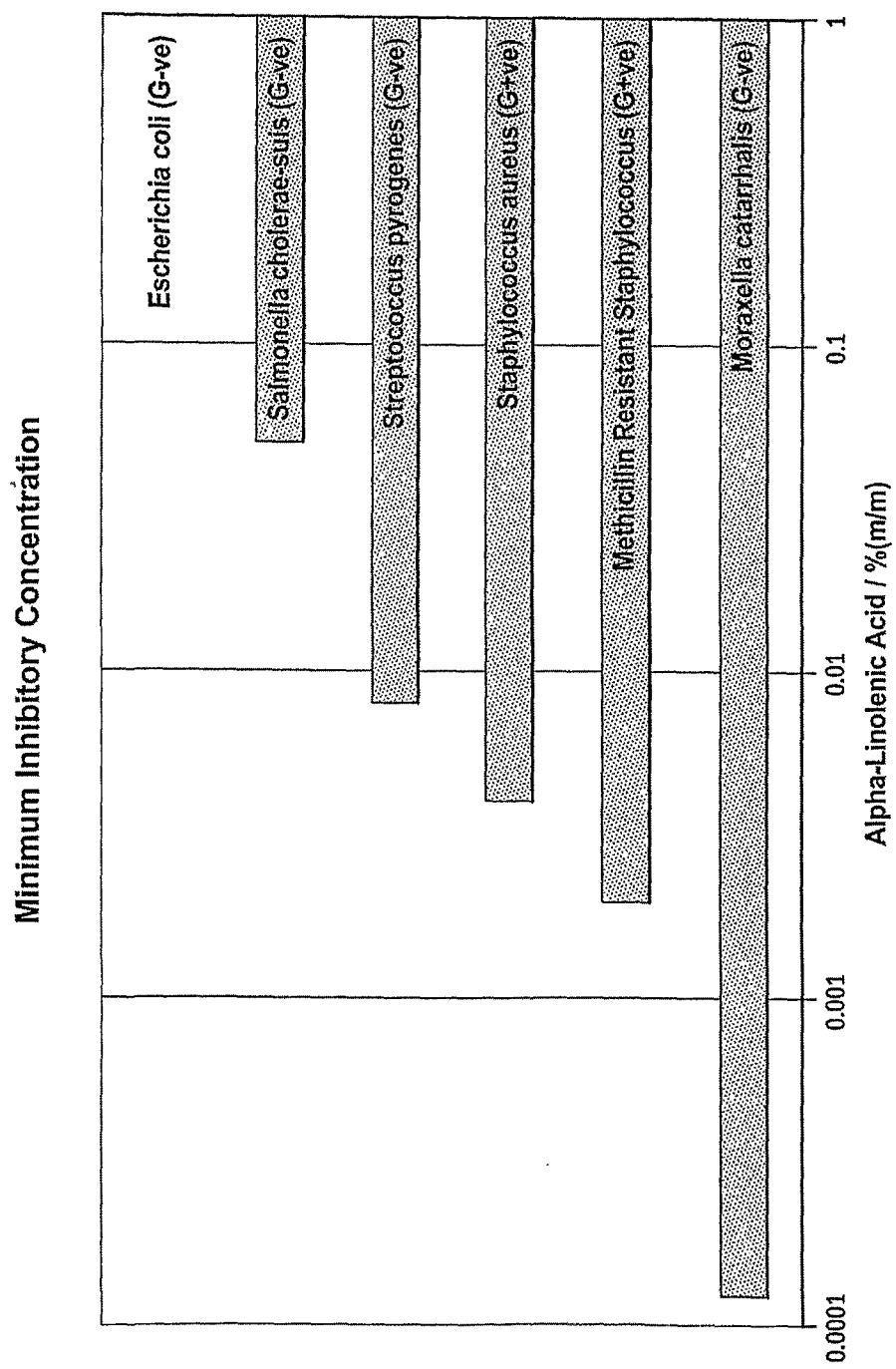
FIG. 3 is a graph showing the minimum concentration of α-linolenic acid required to inhibit growth of a range of microorganisms.

The tests were also performed on *Streptococcus pyogenes*. The results on this microorganism showed a % kill of 87.7% at 30 minutes. Further tests were performed on *Escherichia coli* (G-ve) and *Moraxella catarrhalis* (G-ve). These results are presented in FIGS. 1 and 2 (in two scales—log reduction and % reduction in organism count) with the results of all microorganisms tested in this Example.

EXAMPLE 4

Compositions Comprising α-Linolenic Acid and Terpinen-4-ol

Compositions containing 1% α-linolenic acid and 1% terpinen-4-ol were prepared in the form of a body wash, surface spray, topical ointment, and nasal ointment. The components of the compositions are outlined in Tables 4A, 4B, 4C, and 4D. Melaleucol is a commercially available terpinen-4-ol of a minimum 99% purity, and having a chiral ratio of +/−enantiomers of 1.8:1-2.4:1.

TABLE 4A

| Body Wash | | |
|---|---|---|
| % | gm | Material |
| 3.000 | 30.000 | Cetostearyl Alcohol |
| 5.000 | 50.000 | Sweet Almond Oil |
| 10.000 | 100.000 | Emulgade N1 1000 |
| 2.000 | 20.000 | Glycerol |
| 1.000 | 10.000 | Benzyl Alcohol |
| 1.000 | 10.000 | Cyclomethicone (DC 345) |
| 10.000 | 100.000 | SLES (TEXAPON N25) |
| 10.000 | 100.000 | Betaine (Empigen BS AU) |
| 1.000 | 10.000 | Melaleucol |
| 1.000 | 10.000 | Linolenic Acid |
| 56.000 | 560.000 | Purified Water |
| 100 | 1000 | Total |

TABLE 4B

| Surface Spray | | |
|---|---|---|
| % | gm | Material |
| 5.000 | 50.000 | Cremophor Rh40 |
| 5.000 | 50.000 | Propylene Glycol |
| 0.200 | 2.000 | Benzyl Alcohol |
| 1.000 | 10.000 | Melaleucol |

TABLE 4B-continued

Surface Spray

| % | gm | Material |
|---|---|---|
| 1.000 | 10.000 | Linolenic Acid |
| 87.800 | 878.000 | Purified Water |
| 100 | 1000 | Total |

TABLE 4C

Topical Ointment

| % | gm | Material |
|---|---|---|
| 60.000 | 600.000 | PEG 400 |
| 24.000 | 240.000 | PEG 4000 |
| 14.000 | 140.000 | Propylene Glycol |
| 1.000 | 10.000 | Melaleucol |
| 1.000 | 10.000 | Linolenic Acid |
| 100 | 1000 | Total |

TABLE 4D

Nasal Ointment

| % | gm | Material |
|---|---|---|
| 29.400 | 294.000 | Emulsifying Wax |
| 49.000 | 490.000 | White Soft Parraffin |
| 19.600 | 196.000 | Liquid Paraffin Heavy |
| 1.000 | 10.000 | Melaleucol |
| 1.000 | 10.000 | Linolenic Acid |
| 100.00 | 1000 | Total |

EXAMPLE 5

Antimicrobial Activity of Compositions Comprising α-Linolenic Acid and Terpinen-4-ol The antimicrobial activities of the compositions of Example 4 were subjected to testing. The results presented below show that the compositions are very effective in preventing the growth of Gram positive bacteria, gram negative bacteria and fungi.

The compositions were tested for antimicrobial activity using the suspension test in Example 3 outlined at room temperature against the following organisms:

S. aureus

E. coli

P. aeruginosa

C. albicans

A. niger

N. flavescens

MRSA

The results for the body wash are shown in Tables 5A and 5B.

TABLE 5A

Recovery Results at Different Exposure Times (cfu/mL)

| Test Organisms | Contact Time | | | | Initial Inoculum |
|---|---|---|---|---|---|
| | 30 min | 60 min | 90 min | 120 min | |
| S. aureus | $1.4 \times 10^4$ | $2.8 \times 10^3$ | $2.4 \times 10^3$ | $7.7 \times 10^2$ | $1.7 \times 10^7$ |
| E. coli | 10 | <10 | <10 | <10 | $5.3 \times 10^7$ |
| P. aeruginosa | <10 | <10 | <10 | <10 | $1.7 \times 10^7$ |
| C. albicans | $1.3 \times 10^5$ | $4.6 \times 10^4$ | $4.1 \times 10^4$ | $3.3 \times 10^4$ | $1.6 \times 10^6$ |
| A. niger | $3.2 \times 10^4$ | $2.8 \times 10^4$ | $2.3 \times 10^4$ | $2.3 \times 10^4$ | $2.7 \times 10^6$ |
| N. flavescens | <10 | <10 | <10 | <10 | $1.3 \times 10^6$ |
| MRSA | <10 | <10 | <10 | <10 | $1.5 \times 10^6$ |

CFU = colony forming units
<= Less than

TABLE 5B

Log Reduction at Different Exposure Times ($Log_{10}$)

| Test Organisms | Contact Time | | | |
|---|---|---|---|---|
| | 30 min | 60 min | 90 min | 120 min |
| S. aureus | 3.1 | 3.8 | 3.8 | 4.3 |
| E. coli | 5.9 | >6.7 | >6.7 | >6.7 |
| P. aeruginosa | >6.2 | >6.2 | >6.2 | >6.2 |
| C. albicans | 1.1 | 1.5 | 1.6 | 1.7 |
| A. niger | 1.9 | 2.0 | 2.0 | 2.0 |
| N. flavescens | >5.1 | >5.1 | >5.1 | >5.1 |
| MRSA | >5.2 | >5.2 | >5.2 | >5.2 |

< = Less than
> = Greater than

The results for the surface spray are shown in Tables 6A and 6B.

TABLE 6A

Recovery Results at Different Exposure Times (cfu/mL)

| Test Organisms | Contact Time | | | | Initial Inoculum |
|---|---|---|---|---|---|
| | 30 min | 60 min | 90 min | 120 min | |
| S. aureus | $2.5 \times 10^5$ | $7.0 \times 10^4$ | $2.4 \times 10^4$ | $1.0 \times 10^4$ | $1.7 \times 10^7$ |
| E. coli | $1.7 \times 10^6$ | $1.5 \times 10^6$ | $1.2 \times 10^6$ | $3.2 \times 10^5$ | $5.3 \times 10^7$ |
| P. aeruginosa | $3.7 \times 10^2$ | <10 | <10 | <10 | $1.7 \times 10^7$ |
| C. albicans | $6.3 \times 10^6$ | $3.8 \times 10^4$ | $3.5 \times 10^4$ | $3.6 \times 10^4$ | $1.6 \times 10^6$ |
| A. niger | $4.3 \times 10^4$ | $2.6 \times 10^4$ | $2.9 \times 10^4$ | $2.3 \times 10^4$ | $2.7 \times 10^6$ |
| N. flavescens | <10 | <10 | <10 | <10 | $1.3 \times 10^6$ |
| MRSA | <10 | <10 | <10 | <10 | $1.5 \times 10^6$ |

CFU = colony forming units
<= Less than

TABLE 6B

Log Reduction at Different Exposure Times ($Log_{10}$)

| Test Organisms | Contact Time | | | |
|---|---|---|---|---|
| | 30 min | 60 min | 90 min | 120 min |
| S. aureus | 1.8 | 2.4 | 2.8 | 3.2 |
| E. coli | 1.5 | 1.5 | 1.6 | 2.2 |
| P. aeruginosa | 4.6 | >6.2 | >6.2 | >6.2 |
| C. albicans | 1.4 | 1.6 | 1.7 | 1.6 |
| A. niger | 1.8 | 2.0 | 1.9 | 2.0 |

TABLE 6B-continued

Log Reduction at Different Exposure Times ($Log_{10}$)

| Test Organisms | Contact Time | | | |
|---|---|---|---|---|
| | 30 min | 60 min | 90 min | 120 min |
| N. flavescens | >5.1 | >5.1 | >5.1 | >5.1 |
| MRSA | >5.2 | >5.2 | >5.2 | >5.2 |

< = Less than
> = Greater than

The results for the nasal ointment are shown in Tables 7A and 7B.

TABLE 7A

Recovery Results at Different Exposure Times (cfu/mL)

| Test Organisms | Contact Time | | | | | Initial Inoculum |
|---|---|---|---|---|---|---|
| | 30 min | 60 min | 90 min | 120 min | 24 hr | |
| S. aureus | $1.8 \times 10^3$ | $1.8 \times 10^3$ | $3.4 \times 10^2$ | Contamination | 10 | $3.9 \times 10^6$ |
| E. coli | $1.4 \times 10^4$ | $2.5 \times 10^3$ | $8.4 \times 10^2$ | $6.2 \times 10^2$ | <10 | $1.3 \times 10^7$ |
| P. aeruginosa | $6.0 \times 10^2$ | $1.2 \times 10^3$ | 90 | 60 | <10 | $4.5 \times 10^6$ |
| C. albicans | $1.7 \times 10^2$ | $1.8 \times 10^3$ | $1.5 \times 10^2$ | $1.3 \times 10^2$ | 90 | $1.5 \times 10^6$ |
| A. niger | 70 | 40 | 50 | 20 | <10 | $3.1 \times 10^6$ |
| N. flavescens | <10 | <10 | <10 | <10 | <10 | $1.3 \times 10^6$ |
| MRSA | 60 | <10 | <10 | <10 | <10 | $1.3 \times 10^6$ |

CFU = colony forming units

TABLE 7B

Log Reduction at Different Exposure Times ($Log_{10}$)

| Test Organisms | Contact Times | | | | |
|---|---|---|---|---|---|
| | 30 min | 60 min | 90 min | 120 min | 24 hours |
| S. aureus | 3.3 | 3.3 | 4.1 | Contamination | 5.6 |
| E. coli | 3.0 | 3.7 | 4.2 | 4.3 | >6.1 |
| P. aeruginosa | 3.9 | 4.6 | 4.7 | 4.9 | >5.7 |
| C. albicans | 3.0 | 2.9 | 3.0 | 3.1 | 4.4 |
| A. niger | 4.7 | 4.9 | 4.8 | 5.2 | >5.5 |
| N. flavescens | >5.1 | >5.1 | >5.1 | >5.1 | >5.1 |
| MRSA | 4.3 | >5.1 | >5.1 | >5.1 | >5.1 |

< = Less than
> = Greater than

The results for the topical ointment are shown in Tables 8A and 8B.

TABLE 8A

Recovery Results at Different Exposure Times (cfu/mL)

| Test Organisms | Contact Time | | | | | Initial Inoculum |
|---|---|---|---|---|---|---|
| | 30 min | 60 min | 90 min | 120 min | 24 hr | |
| S. aureus | $1.7 \times 10^4$ | $1.3 \times 10^4$ | $1.6 \times 10^6$ | $1.5 \times 10^4$ | <10 | $3.9 \times 10^6$ |
| E. coli | <10 | <10 | <10 | <10 | <10 | $1.3 \times 10^7$ |
| P. aeruginosa | <10 | <10 | <10 | <10 | <10 | $4.5 \times 10^6$ |
| C. albicans | $2.3 \times 10^3$ | $2.1 \times 10^4$ | $1.4 \times 10^4$ | $1.1 \times 10^4$ | <10 | $1.5 \times 10^6$ |
| A. niger | 80 | 60 | 60 | 20 | <10 | $3.1 \times 10^6$ |
| N. flavescens | <10 | <10 | <10 | <10 | <10 | $1.3 \times 10^6$ |
| MRSA | <10 | <10 | <10 | <10 | <10 | $1.3 \times 10^6$ |

CFU = colony forming units

TABLE 8B

Log Reduction at Different Exposure Times (Log$_{10}$)

| Test Organisms | Contact Times | | | | |
|---|---|---|---|---|---|
| | 30 min | 60 min | 90 min | 120 min | 24 hours |
| S. aureus | 2.4 | 2.5 | 2.4 | 2.4 | >5.6 |
| E. coli | >6.1 | >6.1 | >6.1 | >6.1 | >6.1 |
| P. aeruginosa | >5.7 | >5.7 | >5.7 | >5.7 | >5.7 |
| C. albicans | 2.8 | 1.9 | 2.1 | 2.2 | >5.2 |
| A. niger | 3.6 | 3.7 | 3.7 | 4.2 | >4.5 |
| N. flavescens | >5.1 | >5.1 | >5.1 | >5.1 | >5.1 |
| MRSA | >5.1 | >5.1 | >5.1 | >5.1 | >5.1 |

< = Less than
> = Greater than

EXAMPLE 6

Synergstic Activity of α-Linolenic Acid and Terpinen-4-ol

The anti-microbial activity of a-linolenic acid and terpinen-4-ol separately and in combination were tested using the suspension test as outlined in Example 3 above.

A 1% α-linolenic acid solution in water was prepared to test the activity of this agent alone. This solution was denoted Solution A. The results of the assessment of the recovery of microorganisms following exposure to Solution A for the given time of contact are presented in Table 9A below.

A 1% terpinen-4-ol (specifically, Melaleucol) solution in water was prepared to test the activity of this agent alone. This solution was denoted solution B. The results of the assessment of the recovery of microorganisms following exposure to Solution B for the given time of contact are presented in Table 9B below.

A combination solution was prepared containing 1% α-linolenic acid and 1% terpinen-4-ol (specifically, Melaleucol) in water to test the activity of this combination. This solution was denoted Solution C. The results of the assessment of the recovery of microorganisms following exposure to Solution C for the given time of contact are presented in Table 9C (in terms of surviving organism recovery levels) and Log$_{10}$ reductions.

TABLE 9A

Recovery Results at Different Exposure Times to Solution A composition comprising 1% α-linolenic acid alone

| Test Organisms | Surviving organisms (cfu/mL)/ Log Value | | | | Inoculum cfu/mL |
|---|---|---|---|---|---|
| | Contact Time (Minutes) | | | | |
| | 30 | 60 | 90 | 120 | |
| MRSA | 7.9 × 10$^6$ (6.9) | 1.7 × 10$^6$ (6.2) | 2.1 × 10$^6$ (6.3) | Less than 2.1 × 10$^6$ (<6.3) | 8.0 × 10$^6$ (6.9) |
| S. aureus | 3.6 × 10$^6$ (6.6) | 1.6 × 10$^6$ (6.2) | 1.3 × 10$^6$ (6.1) | Less than 1.3 × 10$^6$ (<6.1) | 3.9 × 10$^6$ (6.6) |
| P. aeruginosa | 2.3 × 10$^6$ (6.4) | 6.6 × 10$^5$ (5.8) | 6.3 × 10$^5$ (5.8) | Less than 6.3 × 10$^5$ (<5.8) | 2.2 × 10$^6$ (6.3) |
| N. flavescens | 1.3 × 10$^5$ (5.1) | 3.7 × 10$^4$ (4.6) | 1.9 × 10$^4$ (4.3) | 6.5 × 10$^2$ (2.8) | 7.5 × 10$^5$ (5.9) |

CFU = colony forming units
<= Less than

TABLE 9B

Recovery Results at Different Exposure Times to Solution B

| Test Organisms | Surviving organisms (cfu/mL)/ Log Value | | | | Inoculum cfu/mL |
|---|---|---|---|---|---|
| | Contact Time (Minutes) | | | | |
| | 30 | 60 | 90 | 120 | |
| MRSA | 1.8 × 10$^5$ (5.3) | 2.6 × 10$^4$ (4.4) | 3.7 × 10$^3$ (3.6) | 9.1 × 10$^2$ (3.0) | 8.0 × 10$^6$ (6.9) |
| S. aureus | 2.0 × 10$^5$ (5.3) | 4.6 × 10$^4$ (4.7) | 2.6 × 10$^4$ (4.4) | 5.2 × 10$^3$ (3.7) | 3.9 × 10$^6$ (6.6) |
| P. aeruginosa | 1.1 × 10$^6$ (6.0) | 4.3 × 10$^5$ (5.6) | 3.9 × 10$^6$ (5.6) | Less than 3.9 × 10$^5$ (<5.6) | 2.2 × 10$^6$ (6.3) |
| N. flavescens | <100 (<2.0) | <100 (<2.0) | <100 (<2.0) | <100 (<2.0) | 7.5 × 10$^5$ (5.9) |

CFU = colony forming units
< = Less than

TABLE 9C

Recovery Results at Different Exposure Times to solution C

| Test Organisms | Surviving organisms (cfu/mL)/ Log Value | | | | Inoculum cfu/mL |
|---|---|---|---|---|---|
| | Contact Time (Minutes) | | | | |
| | 30 | 60 | 90 | 120 | |
| MRSA | 2.0 × 10$^6$ (6.30) | 3.2 × 10$^3$ (5.51) | 1.4 × 10$^3$ (5.15) | 7.4 × 10$^4$ (4.87) | 6.9 × 10$^6$ (6.84) |
| S. aureus | 1.3 × 10$^6$ (6.11) | 1.5 × 10$^3$ (5.18) | 6.6 × 10$^4$ (4.82) | 2.6 × 10$^4$ (4.41) | 4.1 × 10$^6$ (6.61) |
| P. aeruginosa | 5.3 × 10$^4$ (4.72) | 5.0 × 10$^4$ (4.70) | 6.9 × 10$^4$ (4.84) | 5.7 × 10$^4$ (4.76) | 3.5 × 10$^6$ (6.54) |
| N. flavescens | <100 (<2.0) | <100 (<2.0) | <100 (<2.0) | <100 (<2.0) | 6.6 × 10$^6$ (6.82) |

CFU = colony forming units
<= Less than

TABLE 9D

Comparison of Log Reductions (Log 10) Following Exposure to Solution C

| Test Organisms | Contact Time | | | |
|---|---|---|---|---|
| | 30 min | 60 min | 90 min | 120 min |
| MRSA | 0.5 | 1.3 | 1.7 | 2.0 |
| S. aureus | 0.5 | 1.4 | 1.8 | 2.2 |
| P. aeruginosa (ATCC 15442) Results from 0403747 | 0.6 | 0.4 | 0.6 | <0.6 |
| P. aeruginosa (ATCC 9027) | 1.8 | 1.8 | 1.7 | 1.8 |
| N. flavescens | >4.8 | >4.8 | >4.8 | >4.8 |

< = Less than
> = Greater than

It can be seen that both a-linolenic acid and terpinen-4-ol are effective anti-microbial agents. Moreover, it can be seen that there is a synergistic anti-microbial effect between α-linolenic acid and terpinen-4-ol as a 2×log$_{10}$ reduction in the survival of P. aeruginosa was observed after 30 mins, compared with a 1×log$_{10}$ reduction using either α-linolenic acid or terpinen-4-ol separately. This corresponds to a ten-fold increase in antimicrobial effect compared to each component alone, which is greater than the two-fold effect that would follow from the additive effect of the use of the two components.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The claims defining the invention are as follows:

1. A composition comprising:
   α-linolenic acid or an ester thereof, the linolenic acid or ester thereof comprising 1% by weight of the composition, wherein C8-C24 polyunsaturated fatty acids other than α-linolenic acid and esters thereof is not more than 20% on a weight to weight basis compared to the α-linolenic acid or ester thereof present in the composition; and
   a terpinen-4-ol extract of tea-tree oil, at a level of 1% by weight of the composition, wherein the terpinen-4-ol extract contains no more than 20% by weight of the non-terpinen-4-ol components of tea-tree oil.

2. The composition of claim 1, comprising a ratio of C8-C24 polyunsaturated fatty acid or ester thereof to terpinen-4-ol between 1:5 and 5:1.

3. The composition of claim 2, wherein the ratio is between 1:2 and 2:1.

4. The composition of claim 1, wherein the composition is in the form of a lotion, suspension, solution, spray, emulsion, paste, foam, eyewash, ointment, liquid soap, cream, solid soap, mouthwash, pastille or lozenge, gel, a towelette, hair tonic, shampoo or jelly.

5. The composition of claim 4, wherein the composition is in the form of a body wash, surface spray, a towelette, topical ointment, or nasal ointment.

6. The composition of claim 5, wherein the composition comprises between 0.1% and 5% C8-C24 polyunsaturated fatty acid.

7. The composition of claim 5, comprising a pH in the range of 4.8 to 7.5.

8. The composition of claim 1, wherein the composition is a disinfectant composition.

9. A method of inhibiting growth of bacteria, the method comprising the step of contacting a surface with a composition of claim 1.

10. The method of claim 9 wherein the method inhibits the growth of Gram negative and Gram positive bacteria.

11. The method of claim 9, wherein the method inhibits the growth of methicillin-resistant *Staphylococcus aureas*.

12. A method of treating a disease or condition caused by bacteria, the method comprising the step of administering to a subject in need thereof a composition of claim 1, and a carrier.

13. The method of claim 12 wherein the composition is administered topically.

14. The method of claim 12, wherein the method treats a disease or condition caused by methicillin-resistant *Staphylococcus aureas*.

* * * * *